US011452978B2

(12) United States Patent
Iwakai et al.

(10) Patent No.: US 11,452,978 B2
(45) Date of Patent: Sep. 27, 2022

(54) CATALYTIC OXIDATION METHOD AND METHOD FOR PRODUCING CONJUGATED DIENE

(71) Applicant: Mitsubishi Chemical Corporation, Chiyoda-ku (JP)

(72) Inventors: Kazuyuki Iwakai, Tokyo (JP); Hiroki Hinoishi, Tokyo (JP); Hiroshi Kameo, Tokyo (JP); Tetsufumi Yamaguchi, Tokyo (JP)

(73) Assignee: Mitsubishi Chemical Corporation, Chiyoda-ku (JP)

( * ) Notice: Subject to any disclaimer, the term of this patent is extended or adjusted under 35 U.S.C. 154(b) by 0 days.

(21) Appl. No.: 16/570,706

(22) Filed: Sep. 13, 2019

(65) Prior Publication Data

US 2020/0001262 A1    Jan. 2, 2020

Related U.S. Application Data

(63) Continuation of application No. PCT/JP2018/010639, filed on Mar. 16, 2018.

(30) Foreign Application Priority Data

Mar. 17, 2017    (JP) .............................. JP2017-053106

(51) Int. Cl.
   *C07C 5/48*    (2006.01)
   *B01J 8/04*    (2006.01)
   (Continued)

(52) U.S. Cl.
   CPC ............. *B01J 8/0492* (2013.01); *B01J 8/065* (2013.01); *B01J 23/28* (2013.01); *B01J 23/883* (2013.01);
   (Continued)

(58) Field of Classification Search
   CPC ......... C07C 5/48; C07C 5/42; C07C 2521/08; C07C 2523/04; C07C 2523/08; C07C 2523/16
   See application file for complete search history.

(56) References Cited

U.S. PATENT DOCUMENTS 3,236,782 A    2/1966  Koch
3,882,159 A    5/1975  Callahan et al.
(Continued)

FOREIGN PATENT DOCUMENTS

CN    1099024 A    2/1995
CN    1697705 A    11/2005
(Continued)

OTHER PUBLICATIONS

KR20130046458 (A)_English Translation (Year: 2013).*
(Continued)

*Primary Examiner* — Youngsul Jeong
(74) *Attorney, Agent, or Firm* — Oblon, McClelland, Maier & Neustadt, L.L.P.

(57) ABSTRACT

An object of the present invention is to suppress performance deterioration of a molybdenum composite oxide-based catalyst at the time of performing gas-phase catalytic partial oxidation with molecular oxygen by using a tubular reactor. The present invention relates to a catalytic oxidation method using a tubular reactor in which a Mo compound layer containing a Mo compound and a composite oxide catalyst layer containing a Mo composite oxide catalyst are arranged in this order from a reaction raw material supply port side and under a flow of a mixed gas containing 75 vol % of air and 25 vol % of water vapor at 440° C., a Mo sublimation amount of the Mo compound is larger than a Mo sublimation amount of the Mo composite oxide catalyst under the same conditions.

14 Claims, 1 Drawing Sheet

(51) Int. Cl.
*B01J 23/28* (2006.01)
*B01J 8/06* (2006.01)
*B01J 23/883* (2006.01)
*B01J 35/00* (2006.01)

(52) U.S. Cl.
CPC ............ *B01J 35/0006* (2013.01); *C07C 5/48* (2013.01); *B01J 2208/00548* (2013.01); *B01J 2208/00628* (2013.01); *B01J 2208/025* (2013.01); *C07C 2521/08* (2013.01); *C07C 2523/04* (2013.01); *C07C 2523/18* (2013.01); *C07C 2523/28* (2013.01); *C07C 2523/745* (2013.01); *C07C 2523/75* (2013.01); *C07C 2523/755* (2013.01); *C07C 2523/78* (2013.01); *C07C 2523/889* (2013.01)

(56) References Cited

U.S. PATENT DOCUMENTS

| | | | |
|---|---|---|---|
| 4,438,217 A | * | 3/1984 | Takata .................. B01J 23/887 502/205 |
| 4,604,370 A | | 8/1986 | Sarumaru et al. |
| 5,602,280 A | | 2/1997 | Nagai et al. |
| 6,563,000 B1 | | 5/2003 | Yunoki et al. |
| 2005/0033093 A1 | | 2/2005 | Teshigahara et al. |
| 2008/0107583 A1 | | 5/2008 | Teshigahara et al. |
| 2008/0119667 A1 | | 5/2008 | Teshigahara et al. |
| 2008/0286186 A1 | | 11/2008 | Teshigahara et al. |

FOREIGN PATENT DOCUMENTS

| | | | | |
|---|---|---|---|---|
| JP | 47-4042 B2 | 2/1972 | | |
| JP | 59-193136 A | 11/1984 | | |
| JP | 61-33234 A | 2/1986 | | |
| JP | 7-10799 A | 1/1995 | | |
| JP | 7-165663 A | 6/1995 | | |
| JP | 2000-336060 A | 12/2000 | | |
| JP | 2003-146920 A | 5/2003 | | |
| JP | 2003-220335 A | 8/2003 | | |
| JP | 2011-148765 A | 8/2011 | | |
| JP | 2011-178719 A | 9/2011 | | |
| KR | 10-2013-0046458 A | 5/2013 | | |
| KR | 20130046458 A | * | 5/2013 | ............. C07C 5/373 |
| RU | 2 400 298 | 9/2010 | | |
| RU | 2 575 346 | 2/2016 | | |

OTHER PUBLICATIONS

Rodriguez et al. (Reactor designs for ethylene production via ethane oxidative dehydrogenation: Comparison of performance, 2010, I&EC Research, vol. 50, pp. 2690-2697, please refers to Figure 2 in p. 2692) (Year: 2010).*
International Search Report dated May 15, 2018 in PCT/JP2018/010639 filed Mar. 16, 2018 (with English translation).
Written Opinion dated May 15, 2018 in PCT/JP2018/010639 filed Mar. 16, 2018.
Extended European Search Report dated Nov. 29, 2019 in Patent Application No. 18768102.8, 9 pages.
Office Action dated Dec. 17, 2020 in corresponding Indian Patent Application No. 201917037124 (with English-language Translation), citing documents previously submitted, 6 pages.
Office Action dated Jan. 15, 2021, in correspondence Russian Patent Application No. 2019129096 (with English translation).
Office Action dated Nov. 9, 2020 in the corresponding European patent application No. 18766102.6.
Indian Office Action dated Jul. 12, 2021 in Indian Patent Application No. 201917037124, 2 pages.
Office Action dated Mar. 25, 2022 in the corresponding Chinese Patent Application No. 201880018569.7 (with English translation).
Office Action dated Apr. 5, 2022 in the corresponding Japanese patent application No. 2019-506324 and its English machine translation.
Office Action dated Mar. 10, 2022 in the corresponding KR patent application No. 10-2019-7026936 and its English machine translation.

* cited by examiner

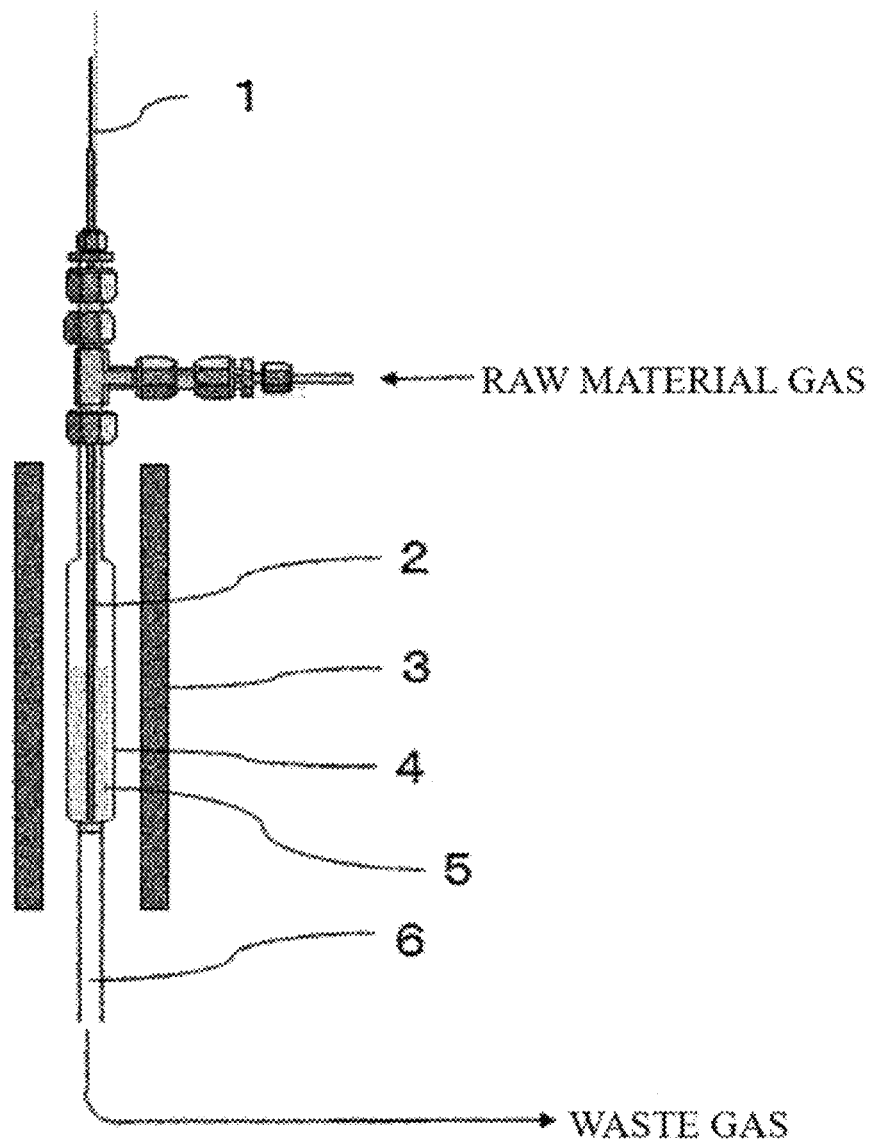

CATALYTIC OXIDATION METHOD AND METHOD FOR PRODUCING CONJUGATED DIENE

TECHNICAL FIELD

The present invention relates to a catalytic oxidation method for performing gas-phase catalytic oxidation with molecular oxygen in a tubular reactor, more specifically, in a fixed-bed multitubular reactor, by using a -composite oxide catalyst containing molybdenum, in which the catalyst is prevented from deterioration due to sublimation of molybdenum.

BACKGROUND ART

In a selective reaction such as gas-phase catalytic oxidation reaction for producing acrolein or methacrolein from propylene, isobutene or tertiary butanol, gas-phase catalytic ammoxidation reaction for producing acrylonitrile or methacrylonitrile from propylene or isobutene, and gas-phase catalytic oxidative dehydrogenation reaction for producing butadiene from butene, a molybdenum bismuth-based composite oxide catalyst is well-known to be a useful catalyst and is industrially widely used in practice.

Examples of the method for producing a conjugated diene such as butadiene by an oxidative dehydrogenation reaction of butenes include a gas-phase catalytic oxidative dehydrogenation reaction according to the following reaction formula:

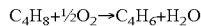

$$C_4H_8 + \tfrac{1}{2}O_2 \rightarrow C_4H_6 + H_2O$$

As for the production of butadiene by gas-phase catalytic oxidative dehydrogenation reaction of n-butene, a method of producing butadiene from butene contained in a mixture containing 1-butene as well as 2-butene, butane, etc. (hereinafter, this mixture is sometimes referred to as "BBSS"), which is obtained by separating butadiene in an extractive distillation column in an extraction separation process of butadiene from a C4 fraction (a mixture of hydrocarbons having 4 carbon atoms; hereinafter sometimes referred to as "BB") produced as a byproduct in naphtha cracking, is performed in industry.

As the catalyst used for this production of butadiene by gas-phase catalytic oxidative dehydrogenation reaction of butene, a composite oxide catalyst containing molybdenum (Mo) and bismuth (Bi) as main components is known to be an effective catalyst. For example, Patent Literature 1 describes a production method for a composite oxide catalyst containing, as essential components, at least one of molybdenum, iron, nickel and cobalt, and silica, which is a composite oxide catalyst for producing butadiene by gas-phase catalytic oxidative dehydrogenation of n-butene with molecular oxygen. In addition, Patent Literature 2 describes a composite oxide catalyst containing, as essential components, molybdenum (Mo), bismuth (Bi) and iron (Fe) and containing, as other essential components, one or more elements selected from nickel (Ni) and cobalt (Co), one or more elements selected from the group consisting of potassium (K), rubidium (Rb) and cesium (Cs), and silica, in which the content of the silica component in the catalyst is from 3 to 10 mass %.

However, the catalyst containing molybdenum has a problem that when the reaction is continued for a long period of time, molybdenum as an essential component sublimates and the catalyst deteriorates over time, leading to a reduction in the reaction activity and selectivity. Regarding a method for obtaining a catalyst having a reduced deterioration rate and a long life, although some proposals have been made, they are incomplete, and sooner or later, the catalyst must be replaced. Accordingly, some methods for regenerating and utilizing a catalyst of which performance is deteriorated have been proposed.

Patent Literature 3 describes a technique where molybdenum is moved (supplied) from an inside of a catalyst to a surface of the catalyst by a method of applying a heat treatment at a temperature of 380 to 540° C. in an atmosphere substantially composed of air and the activity is thereby recovered. In addition, Patent Literature 4 describes a technique for enhancing the butadiene yield by combining two kinds of molybdenum-bismuth catalysts differing in an activity.

BACKGROUND ART LITERATURE

Patent Literature

Patent Literature 1: JP-A-2003-220335
Patent Literature 2: JP-A-2011-178719
Patent Literature 3: JP-A-S61-33234
Patent Literature 4: KR-A-2013-0046458

SUMMARY OF INVENTION

Technical Problem

Meanwhile, it is well known for a long time that one of causes of catalyst deterioration is sublimation of molybdenum, and as the method for regenerating the deteriorated catalyst, a method for replenishing molybdenum in some way is necessary. In the case of a fixed bed, molybdenum needs to be replenished from the upper part of a catalyst layer.

The regeneration method by a heat treatment described in Patent Literature 3 is explained as owing its success to an effect of reoxidizing a metal ion in its reduced state or an effect of restoring the catalyst surface composition having changed due to sublimation of a component such as molybdenum, by the diffusion from a solid interior. However, the regeneration effect by these effects is insufficient, and a portion having a large degree of deterioration, such as gas inlet portion, cannot be completely regenerated, or it is difficult to repeat the regeneration a number of times.

In addition, Patent Literature 4 is silent on the replenishment of molybdenum.

The present invention has been made in consideration of these problems. That is, an object of the present invention is to suppress performance deterioration of a composite oxide-based catalyst containing molybdenum, bismuth, iron, etc. at the time of carrying out gas-phase catalytic partial oxidation with molecular oxygen by using a fixed-bed multitubular reactor.

Means for Solving Problem

The present invention relates to a catalytic oxidation method for performing gas-phase catalytic oxidation with molecular oxygen in a fixed-bed multitubular reactor by using a composite oxide catalyst containing molybdenum, in which a molybdenum compound filling the upper part of a catalyst layer is reacted with water to make a volatile molybdenum compound and thereby prevent the catalyst from deterioration due to sublimation of molybdenum from active components of the catalyst; a production method for an oxidative dehydrogenation reaction product such as conjugated diene; and a production method for an oxidation reaction product such as acrolein and/or acrylic acid.

[1] A catalytic oxidation method of performing a catalytic oxidation reaction by using a tubular reactor in the presence of a molybdenum composite oxide catalyst, wherein:

a molybdenum compound layer containing a molybdenum compound and a composite oxide catalyst layer containing a molybdenum composite oxide catalyst are arranged in this order from a reaction raw material supply port side of the tubular reactor, and under a flow of a mixed gas at 440° C. composed of a composition containing 75 vol % of air and 25 vol % of water vapor, a molybdenum sublimation amount (μg/NL) of the molybdenum compound is larger than a molybdenum sublimation amount (μg/NL) of the molybdenum composite oxide catalyst.

[2] The catalytic oxidation method according to [1], wherein a temperature of the molybdenum compound layer in the catalytic oxidation reaction is equal to or lower than a reaction temperature.

[3] The catalytic oxidation method according to [1] or [2], wherein a difference between the molybdenum sublimation amount of the molybdenum compound and the molybdenum sublimation amount of the molybdenum composite oxide catalyst is from 0.2 to 6 μg/NL.

[4] The catalytic oxidation method according to any one of [1] to [3], wherein 20 mass % or more of the molybdenum compound is molybdenum oxide. [5] A method for producing, from an organic compound, an oxidative dehydrogenation reaction product corresponding to the organic compound by an oxidative dehydrogenation reaction in the presence of a molybdenum composite oxide catalyst by using a tubular reactor, wherein:

a molybdenum compound layer containing a molybdenum compound and a composite oxide catalyst layer containing a molybdenum composite oxide catalyst are arranged in this order from a reaction raw material supply port side of the tubular reactor, and under a flow of a mixed gas at 440° C. composed of a composition containing 75 vol % of air and 25 vol % of water vapor, a molybdenum sublimation amount (μg/NL) of the molybdenum compound is larger than a molybdenum sublimation amount (μg/NL) of the molybdenum composite oxide catalyst.

[6] The method for producing an oxidative dehydrogenation reaction product according to [5], wherein the organic compound is monoolefins having from 4 to 6 carbon atoms and the oxidative dehydrogenation reaction product is a conjugated diene.

[7] A method for producing, from an organic compound, an oxidation reaction product corresponding to the organic compound by an oxidation reaction in the presence of a molybdenum composite oxide catalyst by using a tubular reactor, wherein:

a molybdenum compound layer containing a molybdenum compound and a composite oxide catalyst layer containing a molybdenum composite oxide catalyst are arranged in this order from a reaction raw material supply port side of the tubular reactor, and under a flow of a mixed gas at 440° C. composed of a composition containing 75 vol % of air and 25 vol % of water vapor, a molybdenum sublimation amount (μg/NL) of the molybdenum compound is larger than a molybdenum sublimation amount (μg/NL) of the molybdenum composite oxide catalyst.

[8] The method for producing an oxidation reaction product according to [7], wherein the organic compound is propylene and the oxidation reaction product is at least either one of acrolein and acrylic acid.

[9] A catalytic oxidation method including performing a catalytic oxidation reaction in a tubular reactor in the presence of a composite oxide catalyst containing molybdenum, wherein:

the composite oxide catalyst is divided into two or more catalyst layers, a molybdenum concentration in a catalyst in a catalyst layer closest to a reaction raw material supply port of the tubular reactor is higher than a molybdenum concentration of other catalyst layers, and a temperature during the catalytic oxidation reaction of the catalyst layer closest to a reaction raw material supply port is lower than a temperature during the catalytic oxidation reaction of other catalyst layers.

[10] The catalytic oxidation method according to [9], wherein the temperature of the catalyst layer closest to the reaction raw material supply port is lower than a preset temperature of a heating medium.

[11] The catalytic oxidation method according to [9] or [10], wherein the molybdenum concentration in the catalyst in the catalyst layer closest to the reaction raw material supply port is 1.2 times or more and 3 times or less of a molybdenum concentration in a catalyst in a catalyst layer having a catalyst with a highest molybdenum concentration out of other catalyst layers.

[12] A method for gas-phase catalytic oxidation of olefins, including performing a gas-phase catalytic oxidation of olefins by using the catalytic oxidation method according to any one of [9] to [11], wherein:

the molybdenum amount in the catalyst in the catalyst layer closest to the reaction raw material support port is 5 mass % or more relative to a total amount of molybdenum amounts in the all other catalyst layers.

[13] The method for gas-phase catalytic oxidation of olefins according to [12], wherein 20 mass % or more of the catalyst in the catalyst layer closest to the reaction raw material supply port is molybdenum oxide.

[14] A method for producing a conjugated diene by performing an oxidative dehydrogenation reaction of butenes in the presence of a composite oxide catalyst containing molybdenum by use of a tubular reactor, wherein:

the composite oxide catalyst is divided into two or more catalyst layers, a molybdenum concentration in a catalyst in a catalyst layer closest to a reaction raw material supply port of the tubular reactor is higher than a molybdenum concentration of other catalyst layers, and a temperature during the catalytic oxidation reaction of the catalyst layer closest to the reaction raw material supply port is lower than a temperature during the catalytic oxidation reaction of other catalyst layers.

Effects of Invention

According to the present invention, a catalytic oxidation reaction can be performed with suppressing a molybdenum sublimation loss in a catalyst during the reaction and reducing a decrease in activity of the catalyst.

BRIEF DESCRIPTION OF DRAWINGS

The FIGURE is a schematic diagram illustrating an apparatus used for determining a molybdenum sublimation amount of a molybdenum compound or molybdenum composite oxide catalyst for use in the present invention.

DESCRIPTION OF EMBODIMENTS

Although embodiments of the present invention are described in detail below, the explanation of the constituent features described below is an example (representative example) of the embodiment of the present invention, and the present invention is not limited to these contents as long as its gist is observed.

The present invention relates to a catalytic oxidation method for performing a catalytic oxidation reaction such as gas-phase catalytic oxidation reaction in a tubular reactor in the presence of a catalyst such as a composite oxide catalyst containing molybdenum; a production method for an oxidative dehydrogenation reaction product such as conjugated diene; and a production method for an oxidation reaction product such as acrolein and/or acrylic acid.

<Catalytic Oxidation Reaction>
(Type of Reaction)

The catalytic oxidation method according to the present invention is mainly a gas-phase catalytic oxidation method and is a method used for a reaction from a raw material organic compound to a corresponding oxidation reaction product or oxidative dehydrogenation product. Examples of the reaction to a corresponding oxidation reaction product include a reaction of ethylene to ethylene oxide, a reaction of hydrocarbon having a carbon number of 3 or 4 to an unsaturated aliphatic aldehyde having a carbon number of 3 or 4, and a reaction of a tertiary butanol or an unsaturated aliphatic aldehyde having a carbon number of 3 or 4 to an unsaturated fatty acid having a carbon number of 3 or 4. Furthermore, the reaction includes a reaction of a hydrocarbon having a carbon number of 4 or more, xylene, naphthalene, etc. to a corresponding oxidation reaction product, for example, a reaction to maleic acid, phthalic acid, butadiene, styrene, etc. In addition, the reaction to an oxidative dehydrogenation reaction product includes a reaction of a hydrocarbon having a carbon number of 4 or more to alkenes having 4 or more carbon atoms, such as pentene, methylbutene and dimethylbutene.

Among these, the method is more suitably used in a reaction for producing a corresponding conjugated diene by a gas-phase catalytic oxidative dehydrogenation reaction of olefins, particularly, monoolefins having from 4 to 6 carbon atoms, such as butenes, and in a reaction for producing acrolein and/or acrylic acid by oxidizing propylene.

(Reactor)

Although the reactor is not particularly limited as long as it is a fixed-bed reactor, a tubular reactor, a tank reactor, a plate reactor, etc. are preferred. Among these, a tubular reactor, particularly a multitubular reactor (shell-and-tube reactor), is more preferred.

(Raw Material)

The raw material used differs depending on the above-described type of reaction. The raw material at producing a conjugated diene such as butadiene from butenes by an oxidative dehydrogenation reaction of butenes, and the raw material at producing acrolein and/or acrylic acid by an oxidation reaction of propylene, are described herein.

(1. Raw Material at Producing a Conjugated Diene Such as Butadiene by an Oxidative Dehydrogenation Reaction of Butenes)

As the raw material used in a reaction for producing a conjugated diene such as butadiene by an oxidative dehydrogenation reaction of butenes, a gas containing, as a main component, hydrocarbons having 4 carbon atoms (hereinafter, sometimes simply referred to as "FCC-C4") is produced by Fluid Catalytic Cracking where a heavy oil fraction obtained at the time of distillation of crude oil in a petroleum refining plant, etc. is decomposed using a powdered solid catalyst in a fluidized bed state and converted into a hydrocarbon having a low boiling point, and the gas may be directly used as the raw material gas. In addition, a gas after removing impurities such as phosphorus and arsenic from FCC-C4 may also be used as the raw material gas. The main component as used herein indicates a component that is contained in an amount of usually 40 vol % or more, preferably 60 vol % or more, more preferably 75 vol % or more, still more preferably 99 vol % or more, relative to the raw material gas.

The raw material gas may contain arbitrary impurities within the range wherein the impurities do not inhibit the effects of the present invention.

In a case of producing butadiene from n-butene (1-butene and 2-butene), the impurity which may be contained includes, specifically, a branched monoolefin such as isobutene; a saturated hydrocarbon such as propane, n-butane, i-butane and pentane; an olefin such as propylene and pentene; a diene such as 1,2-butadiene; acetylenes such as methyl acetylene, vinyl acetylene and ethyl acetylene; etc. The amount of the impurity is usually 40 vol % or less, preferably 20 vol % or less, more preferably 10 vol % or less, and still more preferably 1 vol % or less. If this amount is too large, the concentration of 1-butene or 2-butene as the main raw material is decreased and this tends to slow the reaction or reduce the yield of butadiene which is a target product. In the reaction above, the concentration of a linear monoolefin having 4 or more carbon atoms in the raw material gas is not particularly limited but is usually from 50 to 99.99 vol %, preferably from 55 to 99.9 vol %, and more preferably from 60 to 99.9 vol %.

(2. Raw Material at Producing Acrolein and/or Acrylic Acid by an Oxidation Reaction of Propylene)

As a raw material gas used in the reaction for producing acrolein and/or acrylic acid by oxidizing propylene, for example, a propylene component produced by a naphtha cracker of a petroleum refining plant, and a propylene component produced by dehydrogenation of propane, can be used.

The raw material gas may contain arbitrary impurities within the range wherein the impurities do not inhibit the effects of the present invention.

In the case of producing acrolein and/or acrylic acid by using, as a raw material, propylene produced by a naphtha cracker or by dehydrogenation, etc. of propane, the impurity which may be contained includes, specifically, a branched monoolefin such as isobutene; a saturated hydrocarbon such as propane, n-butane, i-butane and pentane; an olefin such as butene and pentene; a diene such as 1,3-butadiene and 1,2-butadiene; acetylenes such as methyl acetylene, vinyl acetylene and ethyl acetylene; etc. The amount of the impurity is usually 40 vol % or less, preferably 20 vol % or less, more preferably 10 vol % or less, and still more preferably 1 vol % or less. If this amount is too large, a concentration of propylene as the main raw material is decreased and this tends to slow the reaction or reduce the yield of acrolein and/or acrylic acid which are the target products. In the reaction above, a concentration of a linear monoolefin having 4 or more carbon atoms in a raw material gas is not particularly limited but is usually from 50 to 99.99 vol %, preferably from 55 to 99.9 vol %, and more preferably from 60 to 99.9 vol %.

The catalytic oxidation method used in the production method of the present invention is characterized in that a molybdenum compound layer containing a molybdenum compound and a composite oxide catalyst layer containing a molybdenum composite oxide catalyst (hereinafter, sometimes referred as "catalyst layer") are arranged in this order from a reaction raw material supply port side of the tubular reactor and furthermore, under a flow of a mixed gas at 440° C. composed of a composition containing 75 vol % of air and 25 vol % of water vapor, a molybdenum sublimation amount of the molybdenum compound (hereinafter, sometimes referred to as "molybdenum sublimation amount of the molybdenum compound") is larger than a molybdenum sublimation amount of the molybdenum composite oxide catalyst (hereinafter, sometimes referred to as "molybdenum sublimation amount of the molybdenum composite oxide catalyst").

According to the present invention, a molybdenum compound having a high molybdenum sublimation amount is packed in the upper part of the molybdenum composite oxide catalyst layer, and sublimation of molybdenum from the molybdenum composite oxide catalyst having a low molybdenum sublimation amount can thereby be suppressed.

(Gas Containing Molecular Oxygen)

In the catalytic oxidation method used in the production method of the present invention, a gas containing molecular oxygen is preferably used. The molecular oxygen-containing gas is a gas containing usually 10 vol % or more, preferably 15 vol % or more, and more preferably 20 vol % or more, of molecular oxygen and, specifically, is preferably air. In this connection, for the reason that costs necessary for industrially preparing the—gas containing molecular oxygen increases, the upper limit of the molecular oxygen content is usually 50 vol % or less, preferably 30 vol % or less, and more preferably 25 vol % or less. In addition, the—gas containing molecular oxygen may contain arbitrary impurities within the range wherein the effects of the present invention are not inhibited.

(Gas Supply)

In the present invention, at the time of supplying the raw material gas to the reactor, it is necessary to mix the raw material gas with the gas containing molecular oxygen and supply the mixed gases (hereinafter, sometimes referred to as "mixed gas") to the reactor. In the mixed gas for use in the present invention, the proportion of the raw material gas is usually 3 vol % or more, preferably 5 vol % or more, and more preferably 6 vol % or more. There is a tendency that as the lower limit value above is larger, a reactor size can be made smaller, leading to a reduction in costs involved in construction and operation. On the other hand, the upper limit is 25 vol % or less, preferably 20 vol % or less, and more preferably 18 vol % or less. As the upper limit value is smaller, a content of substances giving rise to coking on the catalyst, in the raw material gas, is also reduced and therefore, coking of the catalyst is less likely to occur, which is preferable.

A proportion of a linear monoolefin having a carbon umber of 4 or more, such as n-butene (1-butene and/or 2-butene), in the mixed gas is 1 vol % or more, preferably 3 vol % or more, and more preferably 5 vol % or more. On the other hand, the upper limit is 20 vol % or less, preferably 16 vol % or less, and more preferably 14 vol % or less. If this proportion is less than 1 vol %, an amount of the conjugated diene obtained decreases, which is not preferable. In addition, as the proportion is larger, the amount of the conjugated diene obtained increases, while coking is likely to occur, and therefore, the upper limit is more preferably 14 vol % or less.

(Catalytic Oxidation Reaction Conditions)

The catalytic oxidation reaction of the present invention is an exothermic reaction, and the temperature rises by the reaction. However, in the present invention, the reaction temperature is usually adjusted to be from 250 to 450° C., and preferably from 320 to 420° C. As this temperature rises, the catalytic activity tends to be rapidly reduced, and as it lowers, the yield of the conjugated diene, etc. that are the target product is liable to decrease.

The reaction temperature can be controlled using a heating medium (for example, dibenzyltoluene and an inorganic salt such as nitrite, nitrate and a mixture thereof). Note that the reaction temperature as used herein indicates the preset temperature of the heating medium.

In addition, a temperature in the reactor (in the case of a tubular reactor, the temperature in the reaction tube) is not particularly limited but is usually from 250 to 450° C., preferably from 320 to 420° C., and more preferably from 340 to 410° C. In this connection, the temperature in the reactor as used herein is a temperature of the catalyst layer and is a temperature when measured at arbitrary sites of the catalyst layer, and the temperature can be measured, for example, on the reaction tube axis and at the center between the top and bottom of the catalyst layer. The temperature of the catalyst layer can be measured by inserting a thermocouple from the top toward bottom of the catalyst layer.

If the temperature of the catalytic layer exceeds 450° C., this involves a tendency that as the reaction continues, the catalytic activity may be rapidly reduced, whereas if the temperature of the catalytic layer is less than 250° C., the yield of the target product (for example, conjugated diene) tends to decrease. The temperature in the reactor is determined according to the reaction conditions and may be controlled, for example, by the dilution ratio of catalytic layer or the flow rate of mixed gas.

Furthermore, a temperature of the molybdenum compound layer at the time of catalytic oxidation reaction is preferably equal to or lower than the temperature of the catalyst layer. In this case, a phenomenon where molybdenum reacted with water vapor and sublimated from the molybdenum compound layer precipitates in the catalyst layer to clog the reaction tube is less likely to occur. The temperature of the molybdenum compound layer is preferably lower by 3 to 50° C., and more preferably by 5 to 40° C., than the temperature of the catalyst layer.

A pressure in the reactor is not particularly limited but is usually 0 MPaG or more, preferably 0.001 MPaG or more, and more preferably 0.01 MPaG or more. As this value is larger, a larger amount of the reaction gas can be advantageously supplied to the reactor. On the other hand, the upper limit is 0.5 MPaG or less, preferably 0.3 MPaG or less, and more preferably 0.1 MPaG or less. As this value is smaller, the explosion range tends to be narrowed.

The residence time in the reactor in the present invention is not particularly limited, but the lower limit is usually 0.36 seconds or more, preferably 0.8 seconds or more, and more preferably 0.9 seconds or more. As this value is larger, a conversion rate of the monoolefin in the raw material gas is advantageously increased. On the other hand, an upper limit is 3.6 seconds or less, preferably 2.8 seconds or less, and more preferably 2.5 seconds or less. As this value is smaller, the size of the reactor tends to be reduced.

In this connection, in the present invention, a cooling step, a dehydration step, a solvent absorption step, a purification step, etc. may be provided, if desired, as the post-step in the latter part of the reactor.

<Composite Oxide Catalyst Layer Containing Molybdenum Composite Oxide Catalyst>

(Type of Molybdenum Composite Oxide Catalyst)

The molybdenum composite oxide catalyst for use in the present invention includes a composite oxide catalyst containing molybdenum, preferably a composite oxide catalyst containing molybdenum and bismuth, and more preferably a composite oxide catalyst containing molybdenum, bismuth and cobalt. Examples thereof include a composite oxide catalyst represented by the following formula (1):

$$Mo_a Bi_b Co_c Ni_d Fe_e X_f Y_g Z_h Si_i O_j \quad (1)$$

In the formula, X represents at least one element selected from the group consisting of magnesium (Mg), calcium (Ca), zinc (Zn), cerium (Ce) and samarium (Sm), Y represents at least one element selected from the group consisting of sodium (Na), potassium (K), rubidium (Rb), cesium (Cs) and thallium (Tl), Z represents at least one element selected from the group consisting of boron (B), phosphorus (P), arsenic (As) and tungsten (W), a to j represent an atomic ratio of respective elements and when a=12, b to i are in ranges of b=0.5 to 7, c=0 to 10, d=0 to 10 (provided that c+d=1 to 10), e=0.05 to 3, f=0 to 2, g=0.04 to 2, h=0 to 3 and i=5 to 48, and j represents a numerical value satisfying the oxidation state of other elements.

The molybdenum content of the molybdenum composite oxide catalyst is preferably from 15 to 45 mass %, more preferably from 20 to 35 mass %, and still more preferably from 25 to 30 mass %.

(Production Method of Molybdenum Composite Oxide Catalyst)

The molybdenum composite oxide catalysts of the present invention can be produced through a step of integrating and heating supply source compounds of respective component elements constituting the composite oxide catalysts in an aqueous solvent. For example, all of supply source compounds of respective component elements may be integrated and heated in an aqueous system. In this connection, the supply source compounds are compounds containing a predetermined component element and are compounds capable of supplying elements as constituent components of the catalysts at the time of the later-described ripening treatment.

For example, in the case of producing a composite oxide catalyst represented by formula (1), the composite oxide catalyst is preferably produced by a method including a pre-step in which an aqueous solution or aqueous dispersion of the supply source compound containing at least one selected from a group consisting of a molybdenum compound, an iron compound, a nickel compound and a cobalt compound, and silica or a dry matter obtained by drying the aqueous solution or aqueous dispersion is heat-treated to produce a catalyst precursor, and a post-step in which the catalyst precursor, a molybdenum compound and a bismuth compound are integrated together with an aqueous solvent, then dried and fired. When this method is used, the obtained molybdenum composite oxide catalyst exerts high catalytic activity, so that a conjugated diene such as butadiene can be produced at a high yield and a reaction product gas with a small aldehyde content can be obtained. In this connection, the aqueous solvent indicates water, an organic solvent having compatibility with water, such as methanol and ethanol, or a mixture thereof.

A production method for a molybdenum composite oxide catalyst represented by formula (1) is described in detail below.

Firstly, in the production method for this composite oxide catalyst, it is preferred that molybdenum in the catalyst precursor used in the pre-step is molybdenum equivalent to a partial atomic ratio (a1) out of the total atomic ratio (a) of molybdenum in the molybdenum composite oxide catalyst and molybdenum in the molybdenum compound used in the post-step is molybdenum equivalent to the remaining atomic ratio (a2) obtained by subtracting a1 from the total atomic ratio (a) of molybdenum in the molybdenum composite oxide catalyst. The a1 is preferably a value satisfying 1<a1/(c+d+e)<3, and the a2 is preferably a value satisfying 0<a2/b<8. Here, c, d and e represent respectively the total atomic ratio of cobalt, the total atomic ratio of nickel, and the total atomic ratio of iron, in the molybdenum composite oxide catalyst.

The supply source compound for the component element above includes an oxide, a nitrate, a carbonate, an ammonium salt, a hydroxide, a carboxylate, an ammonium carboxylate, an ammonium halide, a hydroacid, an acetylacetonate, an alkoxide, etc. of the component element, and specific examples thereof include the followings.

The molybdenum supply source compound includes ammonium paramolybdate, molybdenum trioxide, molybdic acid, ammonium phosphomolybdate, phosphomolybdic acid, etc.

The iron supply source compound includes ferric nitrate, ferric sulfate, ferric chloride, ferric acetate, etc.

The cobalt supply source compound includes cobalt nitrate, cobalt sulfate, cobalt chloride, cobalt carbonate, cobalt acetate, etc.

The nickel supply source compound includes nickel nitrate, nickel sulfate, nickel chloride, nickel carbonate, nickel acetate, etc.

The silicon supply source compound includes silica, granular silica, colloidal silica, fumed silica, etc.

The bismuth supply source compound includes bismuth chloride, bismuth nitrate, bismuth oxide, bismuth subcarbonate, etc. In addition, the compound may also be supplied as a composite carbonate compound of bismuth and X component or Y component, in which an X component (at least one of Mg, Ca, Zn, Ce and Sm) or a Y component (at least one of Na, K, Rb, Cs and Tl) is caused to form a solid solution.

For example, in the case of using sodium as the Y component, the composite carbonate compound of bismuth and sodium can be produced by adding dropwise and mixing an aqueous solution of a water-soluble bismuth compound such as bismuth nitrate, in an aqueous solution, etc of sodium carbonate or sodium bicarbonate, and washing and drying the obtained precipitate.

In addition, the composite carbonate compound of bismuth and an X component can be produced by adding dropwise and mixing an aqueous solution composed of a water-soluble compound such as bismuth nitrate and nitrate of X component, in an aqueous solution, etc. of ammonium carbonate or ammonium bicarbonate, and washing and drying the obtained precipitate.

When sodium carbonate or sodium bicarbonate is used instead of the ammonium carbonate or ammonium bicarbonate above, a composite carbonate compound of bismuth, sodium and X component can be produced.

Supply source compounds for other component elements include the followings.

The potassium supply source compound includes potassium nitrate, potassium sulfate, potassium chloride, potassium carbonate, potassium acetate, etc.

The rubidium supply source compound includes rubidium nitrate, rubidium sulfate, rubidium chloride, rubidium carbonate, rubidium acetate, etc.

The cesium supply source compound includes cesium nitrate, cesium sulfate, cesium chloride, cesium carbonate, cesium acetate, etc.

The thallium supply source compound includes thallous nitrate, thallous chloride, thallium carbonate, thallous acetate, etc.

The boron supply source compound includes borax, ammonium borate, boric acid, etc.

The phosphorus supply source compound includes ammonium phosphomolybdate, ammonium phosphate, phosphoric acid, phosphorus pentoxide, etc.

The arsenic supply source compound includes ammonium diarseno-18-molybdate, ammonium diarseno-18-tungstate, etc.

The tungsten supply source compound includes ammonium paratungstate, tungsten trioxide, tungstic acid, phosphotungstic acid, etc.

The magnesium supply source compound includes magnesium nitrate, magnesium sulfate, magnesium chloride, magnesium carbonate, magnesium acetate, etc.

The calcium supply source compound includes calcium nitrate, calcium sulfate, calcium chloride, calcium carbonate, calcium acetate, etc.

The zinc supply source compound includes zinc nitrate, zinc sulfate, zinc chloride, zinc carbonate, zinc acetate, etc.

The cerium supply source compound includes cerium nitrate, cerium sulfate, cerium chloride, cerium carbonate, cerium acetate, etc.

The samarium supply source compound includes samarium nitrate, samarium sulfate, samarium chloride, samarium carbonate, samarium acetate, etc.

The aqueous solution or aqueous dispersion of the supply source compound used in the pre-step is an aqueous solution, water slurry or cake containing at least molybdenum (equivalent to a1 out of the total atomic ratio a), iron, at least either nickel or cobalt, and silica.

The aqueous solution or aqueous dispersion of the supply source compound is prepared by integration of supply source compounds in an aqueous system. Here, the integration of supply source compounds in an aqueous system means that aqueous solutions or aqueous dispersions of supply source compounds of respective component elements are at least either mixed or ripened en bloc or stepwise. More specifically, all of (a) a method of mixing respective supply source compounds en bloc, (b) a method of mixing respective supply source compounds en bloc and ripening the mixture, (c) a method of mixing respective supply source compounds stepwise, (d) a method of repeating mixing·ripening of respective supply source compounds stepwise, and a method of combining (a) to (d) are encompassed by the concept of integration of supply source compounds of respective component elements in an aqueous system. Here, the ripening indicates an operation of treating the industrial raw material or half-finished product under specific conditions such as given time and given temperature with an attempt to acquire or raise the required physical properties or chemical properties or allow the progress, etc. of a predetermined reaction. The given time is usually from 10 minutes to 24 hours, and the given temperature is usually from room temperature to the boiling point of the aqueous solution or aqueous dispersion.

A specific method for the integration includes, for example, a method in which an aqueous solution obtained by mixing acidic salts selected from the catalytic components and an aqueous solution obtained by mixing basic salts selected from the catalytic components are mixed, and specific examples thereof include a method of adding, under heating, a mixture containing an iron compound and at least either a nickel compound or a cobalt compound to an aqueous solution of molybdenum compound, and further mixing silica therewith.

The thus-obtained aqueous solution or aqueous dispersion of the supply source compound containing silica is heated at 60 to 90° C. and thereby ripened.

By this ripening, a viscosity of the aqueous solution or aqueous dispersion of the supply source compound is raised, slowing sedimentation of a solid component, and this is effective particularly in preventing disproportionation of components in the next drying step. As a result, the catalytic activity such as raw material conversion rate and selectivity of the molybdenum composite oxide catalyst as the final product are more improved. In addition, at the time of ripening, the aqueous solution or aqueous dispersion of the supply source compound is preferably stirred. The temperature in the ripening is preferably from 60 to 90° C., and more preferably from 70 to 85° C. If the ripening temperature is less than 60° C., the effect of ripening is insufficient, and good activity may not be obtained. On the other hand, if it exceeds 90° C., much water evaporates during the ripening time, and this is disadvantageous to industrial practice. Furthermore, if the ripening temperature exceeds 100° C., a pressure-resistant vessel is required for a dissolution tank, and handling becomes complicated, which is significantly disadvantageous in view of profitability and operability.

The time spent on ripening is preferably from 2 to 12 hours, and more preferably from 3 to 8 hours. If the ripening time is less than 2 hours, an activity and selectivity of the catalyst may not be fully brought out. On the other hand, even if it exceeds 12 hours, the ripening effect is not increased, and this is disadvantageous to industrial practice.

As the stirring method, an arbitrary method can be employed, and examples thereof include a method by a stirrer having a stirring blade, and a method by external circulation using a pump.

The ripened and obtained slurry is heat-treated directly or after drying. In the case of drying the slurry, the drying method and the condition of the obtained dry matter are not particularly limited, and, for example, a powdered dry matter may be obtained using a normal spray drier, slurry drier, drum drier, etc., or a block-like or flake-like dry matter may be obtained using a normal box-type drier or tunnel-type firing furnace. The heat treatment is performed, for example, in air in the temperature region of from 200 to 400° C., and preferably from 250 to 350° C. At this time, the form of the furnace and the method for the treatment are not particularly limited and, for example, heating may be performed using a normal box-type heating furnace, a tunnel-type heating furnace, etc. in a state of the dry matter being fixed, or, heating may be performed using a rotary kiln, etc. with fluidizing the dry matter.

The ignition loss of the catalyst precursor obtained after heat treatment is preferably from 0.5 to 5 mass %, and more preferably from 1 to 3 mass %. By adjusting the ignition loss in this range, a catalyst having high raw material conversion rate or high selectivity can be obtained. In this connection, the ignition loss is a value obtained according to the following formula:

Ignition loss (%)=$[(W_0-W_1)/W_0] \times 100$ $W_0$: Weight (g) after drying the catalyst precursor at 150° C. for 3 hours to remove adhering moisture.

$W_1$: Weight (g) after further heat-treating at 500° C. for 2 hours of the catalyst precursor from which adhering moisture was removed.

In the post-step, integration of the catalyst precursor obtained in the pre-step, a molybdenum compound (a2 equivalent remaining after subtracting a1 equivalent from the total atomic ratio a) and a bismuth compound is performed in an aqueous solvent. At this time, it is preferable to add aqueous ammonia. Addition of X, Y and Z components is also preferably performed in this post-step. The bismuth supply source compound of the present invention is a sparingly water-soluble or water-insoluble bismuth. This compound is preferably used in a powder form. Although these compounds as supply source compounds may be a particle larger than a powder, considering a heating step in which heat should be diffused, smaller particles are preferred. Accordingly, when the compounds as raw materials are not such small particles, pulverization is preferably performed before the heating step.

Next, the obtained slurry is thoroughly stirred and then dried. The dry product obtained in this way is shaped into an arbitrary shape by extrusion molding, tablet molding, carrier molding, and other methods. The shaped product is then subjected to a final heat treatment preferably under the temperature condition of from 450 to 650° C. for approximately from 1 to 16 hours. In this way, a molybdenum composite oxide catalyst having high activity and giving the objective product at a high yield is obtained.

(Composite Oxide Catalyst Layer)

In the present invention, at the time of performing a catalytic oxidation reaction by using a tubular reactor, the molybdenum composite oxide catalyst is packed to form a composite oxide catalyst layer. The composite oxide catalyst layer may contain a component other than the molybdenum composite oxide catalyst, and such a component includes a catalyst which does not contain molybdenum, a solid matter having low reactivity, etc. The solid matter having low reactivity is not particularly limited as long as it is a material having low reactivity with the raw material substance such as monoolefin having 3 or more carbon atoms or with the product such as acrolein and acrylic acid, and, specifically, the solid matter includes a solid matter composed of a ceramic material, etc. such as alumina and zirconia, which is sometimes referred to as an inert ball in general. The shape thereof is not particularly limited and may be any of sphere, cylinder, ring and amorphous. Furthermore, the size thereof is not particularly limited and includes, for example, a size equal to the size of the catalyst, etc. used in the present invention. The content of the molybdenum composite oxide catalyst in the composite oxide catalyst layer is usually from 1 to 99 mass %, preferably from 10 to 90 mass %, and more preferably from 20 to 80 mass %.

In addition, the composite oxide catalyst layer may be composed of two or more layers and is preferably composed of 1 to 3 layers. Here, one composite oxide catalyst layer means a continuous layer containing the molybdenum composite catalyst and having the same layer composition.

<Molybdenum Compound Layer>

(Type of Molybdenum Compound)

The molybdenum compound for use in the present invention is a compound containing molybdenum. The molybdenum compound includes a compound containing oxygen, such as ammonium paramolybdate, molybdenum oxide, molybdic acid, ammonium phosphomolybdate and phosphomolybdic acid, a mixture thereof, etc. and a commercially available product can also be used. However, a molybdenum compound having a larger molybdenum sublimation amount (μg/NL) than the molybdenum sublimation amount (μg/NL) of the molybdenum composite oxide catalyst used in the composite oxide catalyst layer needs to be used. In view of quantitative balance between the replenishment amount and sublimation amount of molybdenum in the catalyst layer, a difference between the molybdenum sublimation amount (μg/NL) of the molybdenum compound and the molybdenum sublimation amount (μg/NL) of the molybdenum composite oxide catalyst is preferably from 0.1 to 10 μg/NL, and more preferably from 0.2 to 6 μg/NL.

The molybdenum compound preferably contains molybdenum oxide ($MoO_3$) in an amount of 20 mass % or more, and more preferably 30 mass % or more, and preferably in an amount of less than 100 mass %, and more preferably 90 mass % or less.

The molybdenum sublimation amount as used in the present invention is the amount (μg/NL) of molybdenum (Mo) sublimated under a flow of a mixed gas at 440° C. composed of a composition containing 75 vol % of air and 25 vol % of water vapor and is the amount (μg/NL) of sublimated molybdenum (Mo) determined, for example, by the method described below.

(Molybdenum Sublimation Amount)

In an apparatus illustrated in the FIGURE, a molybdenum compound or molybdenum composite oxide catalyst (sometimes simply referred to as a composite oxide catalyst) 5 is packed at room temperature of 25° C. into a glass-made reaction tube 4 having an inner diameter of 6 mm, and the temperature inside the reaction tube is kept at 440° C. by heating, the reaction tube by an electric heater 3. Subsequently, a mixed gas composed of a composition containing 75 vol % of air and 25 vol % of water vapor is continuously supplied to the reaction tube at $1.0 \times 10^3$ NL/hr for 10 hours, and a precipitate deposited and attached to the lower part 6 of the glass-made reaction tube is dissolved with an aqueous ammonia solution to make a solution. The solution is put in a beaker and gently evaporated to dryness at 250° C., and the obtained solid is, after adding 0.2 mL of sulfuric acid and ion exchanged water thereto, dissolved under warming. Thereafter, the resulting solution is diluted to 25 mL with ion-exchanged water, and the Mo amount (g) in the diluted solution is analyzed by means of an inductively coupled plasma emission spectrometer. The Mo amount (g) obtained by the analysis is divided by the amount of gas flowed ($1.0 \times 10^3$ NL/hr×10 hours), and the molybdenum amount (g/NL) per unit gas flow rate is thereby determined and defined as the molybdenum sublimation amount.

[Measurement Conditions of Inductively Coupled Plasma Emission Spectrometer]

Apparatus: iCAP6500 Duo, manufactured by Thermo Fisher Scientific K.K.

Analysis line: Mo 202.030 nm

Plasma output: 1,150 W

Plasma: axial

In this connection, molybdenum in the molybdenum compound and molybdenum composite oxide catalyst 5 reacts with water vapor in the mixed gas (gas) warmed by the electric heater 3 and is sublimated as $MoO_2(OH)_2$ in the glass-made reaction tube 4. The sublimated $MoO_2(OH)_2$ flows out of a system from the lower part 6 of the glass-made reaction tube. However, since the lower part of the reaction tube is not heated by the electric heater and is naturally cooled at room temperature, Mo in the sublimated $MoO_2$ (OH)$_2$ turns into MoO$_3$ and precipitates in the lower part of the reaction tube. When the components of the waste gas were examined, Mo was not detected. Accordingly, all Mo in MoO$_2$(OH)$_2$ is regarded as turned into MoO$_3$ and precipitated, so that the amount (g/NL) of sublimated Mo can be determined from the amount of precipitated MoO$_3$.

In addition, the molybdenum compound preferably contains an alkali metal or an alkaline earth metal so as to lower its activity. In particular, the activity of the molybdenum compound is preferably lowered to prevent reaction with a component contained in the raw material gas. The alkali metal includes sodium, potassium, rubidium, cesium, etc. The alkaline earth metal includes magnesium, calcium, etc.

The sodium supply source compound includes sodium nitrate, sodium sulfate, sodium chloride, sodium carbonate, sodium acetate, etc.

The potassium supply source compound, rubidium supply source compound, cesium supply source compound, magnesium supply source compound, and calcium supply source compound include those described above.

Molybdenum in the molybdenum compound reacts with water vapor and is sublimated into gas phase and therefore, in order to enhance the contact efficiency with water vapor, it is also preferred that the molybdenum compound is supported on a support such as silica, alumina and titania and used. In this case, the molybdenum compound including the support is regarded as the molybdenum compound.

The molybdenum compound containing an alkali metal or an alkaline earth metal or the molybdenum compound further supported on a carrier can be produced through a step of integrating and heating supply source compounds for respective component elements constituting the molybdenum compound in an aqueous solvent, similarly to the production of the molybdenum composite oxide catalyst.

The molybdenum content of the molybdenum compound is preferably 20 mass % or more, more preferably 25 mass % or more, and particularly preferably 30 mass % or more. When a large amount of molybdenum is contained in the molybdenum compound, molybdenum can be supplied to the composite oxide catalyst layer over a long period of time.

In addition, the molybdenum content of the molybdenum compound is preferably larger than the molybdenum content of the molybdenum composite oxide catalyst in the composite oxide catalyst layer. In particular, the molybdenum content is preferably 1.2 times or more, and more preferably 1.5 times or more, of the largest molybdenum content of the molybdenum composite oxide catalyst. When the molybdenum content is 1.2 times or more, molybdenum can be supplied to the molybdenum composite oxide catalyst layer over the long term and therefore, the catalytic oxidation reaction can continue over the long term. On the other hand, the upper limit is preferably 3.0 times, and more preferably 2.0 times.

(Molybdenum Compound Layer)

The molybdenum compound layer may contain other compounds such as inert ball described above, besides the molybdenum compound having a larger molybdenum sublimation amount than the molybdenum sublimation amount of the molybdenum composite oxide catalyst.

The content of the molybdenum compound of the molybdenum compound layer is 20 mass % or more, preferably 60 mass % or more, more preferably 80 mass % or more, still more preferably 95 mass % or more, and particularly preferably 100 mass %.

Furthermore, the molybdenum content in the molybdenum compound layer is preferably 5 mass % or more, and more preferably 20 mass % or more, relative to the total amount of molybdenum contents in respective composite oxide catalyst layers. When the content is 5 mass % or more, the effect of reducing a decrease in activity due to Mo sublimation of the molybdenum composite oxide catalyst can be sufficiently exerted.

On the other hand, an upper limit is preferably 100 mass % or less, and more preferably 50 mass % or less. If the content exceeds 100 mass %, the molybdenum compound layer becomes too long, and this leads to a large reactor, which is not preferable.

A temperature of the molybdenum compound layer during the catalytic oxidation reaction is preferably equal to or lower than the above-described reaction temperature. If the temperature of the molybdenum compound layer is higher than the reaction temperature, there is more likely to occur a phenomenon where molybdenum is sublimated as molybdenum hydroxide (MoO$_2$(OH)$_2$) from the molybdenum compound layer, cooled and precipitated downstream of the molybdenum compound layer (the raw material inlet side is denoted as upstream) and turns into molybdenum oxide (MoO$_3$) and furthermore, the carbon accumulates (coking) starting at the molybdenum oxide to clog the reaction tube. The temperature of the molybdenum compound layer is preferably lower by 0 to 40° C., and more preferably by 0 to 20° C., than the reaction temperature, In this connection, since the catalytic oxidation reaction of the present invention is an exothermic reaction, when the molybdenum compound layer contains a substance having high activity to the catalytic oxidation reaction, the temperature of the molybdenum compound layer is usually higher than the reaction temperature. Accordingly, it is preferable to use, as the molybdenum compound, a compound having low activity, preferably having no activity, to the catalytic oxidation reaction of the present invention. The technique for reducing the activity of the molybdenum compound includes, as described above, a method of incorporating an alkali metal or an alkaline earth metal into the molybdenum compound. For the same reason, in the case where the molybdenum compound layer contains a compound other than the molybdenum compound the compound includes a compound having low activity, preferably, having no activity, to the catalytic oxidation reaction of the present invention, furthermore, having low reactivity with the raw material substance, oxygen and water vapor, and preferably having no reaction thereto. Such a compound includes the above-described inert ball, etc.

In this connection, the temperature of the molybdenum compound layer is a temperature in measurement at arbitrary sites of the molybdenum compound layer, and the temperature can be measured, for example, at a site on the reaction tube axis and in the lowermost part of the molybdenum compound layer. The temperature of the molybdenum compound layer can be measured by inserting a thermocouple from the top toward bottom of the molybdenum compound layer.

<Other Layers>

In the present invention, the reaction tube may have therein an inert layer composed of the above-described inert ball, etc., besides the composite oxide catalyst layer and the molybdenum compound layer. Note that the inert layer as used herein is, as described above, a layer being inactive to the catalytic oxidation reaction of the present invention and having no reaction to the raw material substance, oxygen, water vapor, product gas, etc.

EXAMPLES

Although the present invention is described in greater detail below by referring to Examples, the present invention is not limited by the following Examples.

<Preparation of Molybdenum Composite Oxide Catalyst>

Under warming at 70° C., 54 g of ammonium paramolybdate was dissolved in 250 ml of pure water. Subsequently, 7.18 g of ferric nitrate, 31.8 g of cobalt nitrate, and 31.8 g of nickel nitrate were dissolved in 60 mL of pure water under warming at 70° C. These solutions were gradually mixed with stirring thoroughly.

Thereafter, 64 g of silica was added, and the mixture was thoroughly stirred to obtain a slurry. The slurry was warmed at 75° C. and ripened for 5 hours. The slurry was then dried by heating and furthermore, subjected to a heat treatment at 300° C. for 1 hour in an air atmosphere.

The obtained particulate solid (ignition loss: 1.4 mass %) of the catalyst precursor was ground, and a slurry was obtained by dispersing 40.1 g of ammonium paramolybdate in a solution prepared by adding and dissolving 10 ml of aqueous ammonia in 150 ml of pure water. Subsequently, 0.85 g of borax and 0.36 g of potassium nitrate were dissolved in 40 ml of pure water under warming at 25° C., and the slurry above was added thereto.

Furthermore, 58.1 g of bismuth subcarbonate containing 0.45% Na in the form of solid solution was added and mixed with stirring. The resulting slurry was dried by heating at 130° C. for 12 hours, and the obtained particulate solid was tablet-formed into a tablet of 5 mm in diameter and 4 mm in height by using a small molding machine and then fired at 500° C. for 4 hours to obtain a catalyst. The catalyst calculated from the charged raw materials was a molybdenum composite oxide having the following atomic ratio.

Mo:Bi:Co:Ni:Fe:Na:B:K:Si=12:5:2.5:2.5:0.4:0.35:0.2:0.08:24

In this connection, the molybdenum concentration of the obtained molybdenum composite oxide was analyzed and found to be 27.8 mass %.

(Molybdenum Sublimation Amount of Molybdenum Composite Oxide Catalyst)

In an apparatus illustrated in the FIGURE, 0.8 g of the molybdenum composite oxide catalyst prepared above was packed at room temperature of 25° C. into a glass-made reaction tube having an inner diameter of 6 mm, and the temperature inside the reaction tube was kept at 440° C. by heating the reaction tube by an electric heater. Subsequently, a mixed gas composed of a composition containing 75 vol % of air and 25 vol % of water vapor was continuously supplied to the reaction tube at $1.0 \times 10^3$ NL/hr for 10 hours, and a precipitate deposited and attached to the lower part of the reaction tube was dissolved with an aqueous ammonia solution to make a solution. The solution was put in a beaker and gently evaporated to dryness at 250° C. and the obtained solid was, after adding 0.2 mL of sulfuric acid and ion exchanged water thereto, dissolved under warming. Thereafter, the resulting solution was diluted to 25 mL with ion-exchanged water, and the Mo amount (g) in the diluted solution was analyzed by means of an inductively coupled plasma emission spectrometer. The Mo amount (g) obtained by the analysis was divided by the amount of gas flowed ($1.0 \times 10^3$ NL/hr×10 hours), and the molybdenum amount (g/NL) per unit gas flow rate was thereby determined and defined as the molybdenum sublimation amount.

[Measurement Conditions of Inductively Coupled Plasma Emission Spectrometer]

Apparatus: iCAP6500 Duo, manufactured by Thermo Fisher Scientific K.K.

Analysis line: Mo 202.030 nm

Plasma output: 1,150 W

Plasma: axial

In this connection, molybdenum in the molybdenum composite oxide catalyst reacts with water vapor in a mixed gas warmed by the electric heater and is sublimated as $MoO_2(OH)_2$ in a glass-made reaction tube. The sublimated $MoO_2(OH)_2$ flows out of the system from the lower part of the glass-made reaction tube. However, since the lower part of the reaction tube is not heated by the electric heater and is naturally cooled at room temperature, Mo in the sublimated $MoO_2(OH)_2$ turns into $MoO_3$ and precipitates in the lower part of the reaction tube. When components of waste gas were examined, Mo was not detected. Accordingly, all Mo in $MoO_2(OH)_2$ is regarded as turned into $MoO_3$ and precipitated, so that an amount (g/NL) of sublimated Mo can be determined from the amount of precipitated $MoO_3$.

Reference Example 1

The molybdenum composite oxide catalyst prepared above was packed into 113 reaction tubes (length: 3,500 mm, inner diameter: 27 mm, material: SUS304) of a multitubular fixed-based reactor, and production of butadiene by an oxidative hydrogenation reaction of butene was conducted. The pressure inside the reaction tube was set to 0.05 MPaG, and BBSS having a component composition shown in Table 1, air, nitrogen and water vapor were supplied at flow rates of $15.7 \times 10^3$ NL/hr, $81.7 \times 10^3$ NL/hr, $62.5 \times 10^3$ NL/hr and $17.7 \times 10^3$ NL/hr, respectively, heated at 214° C. by a preheater, and then supplied to the multitubular reactor through the raw material gas inlet. A temperature was adjusted by flowing a heating medium at a temperature of 380° C. to the barrel side of the reactor such that a maximum temperature inside the reaction tube becomes 415 to 420° C.

After performing a continuous operation for 3,700 hours with withdrawing a product gas containing butadiene of an obtained composition of Table 2 from the product gas outlet, the reaction was stopped, and a molybdenum composite oxide was withdrawn.

(Molybdenum Sublimation Amount of Molybdenum Composite Oxide Catalyst after Catalytic Oxidation Reaction)

A molybdenum sublimation amount of the molybdenum composite oxide catalyst after performing an oxidative dehydrogenation reaction (catalytic oxidation reaction) for 3,700 hours was determined in the same manner as the molybdenum sublimation amount of the molybdenum composite oxide catalyst after the preparation above and found to be 1.2 μg/NL.

TABLE 1

| Component Name | Composition (mol %) |
| --- | --- |
| n-Butane | 15.2 |
| i-Butene | 1.6 |
| 1-Butene | 26.1 |
| Cis-2-butene | 26.7 |
| Trans-2-butene | 26.8 |
| Other components | 3.6 |

TABLE 2

| Component Name | Composition (mol %) |
|---|---|
| 1,3-Butadiene | 4.8 |
| Oxygen | 4.7 |
| Nitrogen | 67.2 |
| $H_2O$ | 16.34 |
| Other components | 6.96 |

TABLE 3

| Component Name | Composition (mol %) |
|---|---|
| n-Butane | 21.8 |
| i-Butene | 0.6 |
| 1-Butene | 0.6 |
| Cis-2-butene | 27.4 |
| Trans-2-butene | 49.4 |
| Other components | 0.2 |

<Preparation of Molybdenum Compound Used in Molybdenum Compound Layer>

In 200 g of water, 85.57 g of ammonium paramolybdate and 2.44 g of potassium nitrate were dissolved, and 29.1 g of silica was further mixed. The mixture was then dried by heating to obtain a solid composed of a molybdenum compound containing molybdenum oxide, potassium and silica. By using a small molding machine, 40 g of the solid obtained by heating and drying was tablet-formed into a tablet of 5 mm in diameter and 4 mm in height. The molybdenum concentration of the obtained solid material was analyzed and found to be 46.5 mass %. In addition, the content rate of molybdenum oxide in the obtained solid material was 69.7 mass %.

(Molybdenum Sublimation Amount of Molybdenum Compound)

The molybdenum sublimation amount of the molybdenum compound prepared above was determined in the same manner as in the case of the molybdenum composite oxide catalyst and found to be 7.0 μg/NL.

Example 1

In a stainless steel-made reaction tube having an inner diameter of 10 mm and a length of 500 mm, inert balls (in the form of a sphere having a diameter of 2 mm) were previously packed (packed layer length: 140 mm), and 1 g of a molybdenum composite oxide catalyst after a reaction for 3,700 hours, which was withdrawn from a multitubular fixed-bed reactor after an oxidative dehydration reaction in Reference 1, was packed on the inert ball packed layer to form a composite oxide catalyst layer. After packing inert balls on the composite oxide catalyst layer, 1 g of the molybdenum compound prepared in <Preparation of Molybdenum Compound Used in Molybdenum Compound Layer> was packed to form a molybdenum compound layer. In this connection, the molybdenum residual ratio in the composite oxide catalyst after a reaction for 3,700 hours was measured by XRF (manufactured by Nippon Thermonics Co., Ltd., Model NT-210) and found to be 90.1%.

Next, an inorganic salt containing nitrite and nitrate was used as a heating medium, and the temperature of the heating medium was set to 390° C.

The pressure inside the reaction tube was adjusted to 0.05 MPaG, and nitrogen at 2.00 NL/hr, air at 3.36 NL/hr, and water vapor at 2.00 NL/hr were previously supplied to a preheater. Thereafter, BBSS shown in Table 1 as the raw material gas was supplied at 0.64 NL/hr and mixed in the preheater, and the temperature of the resulting mixed gas was raised to 345° C. Subsequently, an oxidative dehydrogenation reaction was performed by continuously supplying the mixed gas at 8.00 NL/hr from the top of the reaction tube, and the product gas was withdrawn from the bottom of the reaction tube.

In this connection, a temperature of the catalyst layer (a temperature on the reaction tube axis and at the center between the top and bottom of the catalyst layer) during reaction was measured by a sheath thermocouple in an insertion tube having an outer diameter of 2.0 mm provided at the center of the reaction tube and found to be 409° C. In addition, a temperature of the molybdenum compound layer (a temperature at a site on the reaction tube axis and in the lowermost part of the molybdenum compound layer) was measured in the same manner and found to be 377° C. A conversion rate of n-butene at 120 hours after the initiation of reaction was 85.7%, and a conversion rate of n-butene after 1,968 hours was 75.4%. A molybdenum residual ratio in the molybdenum composite oxide catalyst withdrawn after the reaction was measured by XRF and found to be 92.2%.

Example 2

In a stainless steel-made reaction tube having an inner diameter of 10 mm and a length of 500 mm, inert balls (in the form of a sphere having a diameter of 2 mm) were previously packed (packed layer length: 140 mm), and 1 g of the molybdenum composite oxide catalyst prepared in <Preparation of Molybdenum Composite Oxide Catalyst> was packed on the inert ball packed layer to form a composite oxide catalyst layer. After packing inert balls on the catalyst layer, 1 g of the molybdenum compound prepared in <Preparation of Molybdenum Compound Used in Molybdenum Compound Layer> was packed to form a molybdenum compound layer.

An inorganic salt containing nitrite and nitrate was used as a heating medium, and a temperature of the heating medium was set to 390° C.

The pressure inside the reaction tube was adjusted to 0.05 MPaG, and nitrogen at 2.16 NL/hr, air at 3.25 NL/hr, and water vapor at 2.00 NL/hr were previously supplied to a preheater. Thereafter, a gas shown in Table 3 as the raw material gas was supplied at 0.67 NL/hr and mixed in the preheater, and a temperature of the resulting mixed gas was raised to 345° C.

Subsequently, an oxidative dehydrogenation reaction was performed by continuously supplying the mixed gas at 8.00 NL/hr from the top of the reaction tube, and a product gas was withdrawn from the bottom of the reaction tube.

In this connection, a temperature of the catalyst layer (a temperature on the reaction tube axis and at the center between the top and bottom of the catalyst layer) during reaction was measured by a sheath thermocouple in an insertion tube having an outer diameter of 2.0 mm provided at the center of the reaction tube and found to be 401° C. In addition, the temperature of the molybdenum compound layer (the temperature at a site on the reaction tube axis and in the lowermost part of the molybdenum compound layer) was measured in the same manner and found to be 376° C.

A conversion rate of n-butene at 336 hours after the initiation of reaction was 88.9%, and a conversion rate of n-butene after 2,544 hours was 87.4%. A molybdenum residual ratio in the molybdenum composite oxide catalyst withdrawn after the reaction was measured by XRF and found to be 96.1%.

Comparative Example 1

This was conducted thoroughly in the same manner as in Example 1 except that the molybdenum compound was not packed as the molybdenum compound layer. A conversion rate of n-butene at 120 hours after the initiation of reaction was 85.3%, and a conversion rate of n-butene after 1,968 hours was 72.7%. A molybdenum residual ratio in the molybdenum composite oxide catalyst withdrawn after the reaction was measured by XRF and found to be 88.7%.

Comparative Example 2

This was conducted thoroughly in the same manner as in Example 2 except that the molybdenum compound was not packed as the molybdenum compound layer. A conversion rate of n-butene at 336 hours after the initiation of reaction was 88.9%, and a conversion rate of n-butene after 2,544 hours was 85.0%. A molybdenum residual ratio in the molybdenum composite oxide catalyst withdrawn after the reaction was measured by XRF and found to be 94.2%.

TABLE 4

| | Conditions | | After Oxidative Dehydrogenation Reaction | | | | |
|---|---|---|---|---|---|---|---|
| | Mo Compound Layer | Mo Composite Oxide Catalyst Layer | Conversion Rate of n-Butene After 120 Hours | Conversion Rate of n-Butene After 336 Hours | Conversion Rate of n-Butene After 1,968 Hours | Conversion Rate of n-Butene After 2,544 Hours | Mo Residual Ratio of Mo Composite Oxide Catalyst |
| Example 1 | Sublimation amount of Mo compound: 7.0 μg/NL | Sublimation amount of Mo composite oxide catalyst: 1.2 μg/NL | 85.7% | — | 75.4% | — | 92.2% |
| Example 2 | Sublimation amount of Mo compound: 7.0 μg/NL | Sublimation amount of Mo composite oxide catalyst: 6.7 μg/NL | — | 88.9% | — | 87.4% | 96.1% |
| Comparative Example 1 | — | Sublimation amount of Mo composite oxide catalyst: 1.2 μg/NL | 85.3% | — | 72.2% | — | 88.7% |
| Comparative Example 2 | — | Sublimation amount of Mo composite oxide catalyst: 6.7 μg/NL | — | 88.9% | — | 85.0% | 94.2% |

While the invention has been described in detail and with reference to specific embodiments thereof, it will be apparent to one skilled in the art that various changes and modifications can be made therein without departing from the spirit and scope of the invention. This application is based on Japanese Patent Application (Patent Application No. 2017-053106) filed on Mar. 17, 2017, the contents of which are incorporated herein by way of reference.

REFERENCE SIGNS LIST

1. Temperature indicator
2. Temperature indicator insertion tube
3. Electric heater
4. Glass-made reaction tube
5. Molybdenum compound or composite oxide catalyst
6. Lower part of glass-made reaction tube

The invention claimed is:

1. A method of performing a catalytic oxidation reaction in a tubular reactor in the presence of a molybdenum composite oxide catalyst, the method comprising:
   arranging a molybdenum compound layer containing a molybdenum compound and a composite oxide catalyst layer containing a molybdenum composite oxide catalyst in this order from a reaction raw material supply port side of the tubular reactor; and
   feeding a raw material comprising an organic compound into the tubular reactor,
   wherein the molybdenum compound layer supplies molybdenum to the composite oxide catalyst layer,
   wherein the catalytic oxidation reaction comprises an oxidation reaction for producing, from the organic compound under a reaction temperature, an oxidation reaction product corresponding to the organic compound,
   wherein a temperature of the molybdenum compound layer at the time of the catalytic oxidation reaction is lower by 3 to 50° C. than a temperature of the catalyst layer,
   wherein the temperature of the molybdenum compound layer at the time of catalytic oxidation reaction is lower by greater than 0° C. to 40° C. than the reaction temperature,
   wherein the molybdenum compound comprises molybdenum oxide and an alkali metal or an alkaline earth metal, and
   wherein, under a flow of a mixed gas at 440° C. composed of a composition containing 75 vol % of air and 25 vol % of water vapor, a molybdenum sublimation amount (μg/NL) of the molybdenum compound is larger than a molybdenum sublimation amount (μg/NL) of the molybdenum composite oxide catalyst.

2. The method according to claim 1, wherein a difference between the molybdenum sublimation amount of the molybdenum compound and the molybdenum sublimation amount of the molybdenum composite oxide catalyst is from 0.2 to 6 μg/NL.

3. The method according to claim 1, wherein 20 mass % or more of the molybdenum compound is molybdenum oxide.

4. The method according to claim 1, wherein the catalytic oxidation reaction comprises an oxidation reaction for producing, from the organic compound, an oxidation reaction product corresponding to the organic compound.

5. The method according to claim 4, wherein the organic compound is propylene and the oxidation reaction product is at least either one of acrolein and acrylic acid.

6. A method of performing a catalytic oxidation reaction in a tubular reactor in the presence of a molybdenum composite oxide catalyst, the method comprising:

arranging a molybdenum compound layer containing a molybdenum compound and a composite oxide catalyst layer containing a molybdenum composite oxide catalyst in this order from a reaction raw material supply port side of the tubular reactor; and feeding a raw material comprising an organic compound into the tubular reactor, wherein the molybdenum compound layer supplies molybdenum to the composite oxide catalyst layer, wherein the catalytic oxidation reaction comprises an oxidative dehydrogenation reaction for producing, from the organic compound under a reaction temperature, an oxidative dehydrogenation reaction product corresponding to the organic compound, wherein a temperature of the molybdenum compound layer at the time of the catalytic oxidation reaction is lower by 3 to 50° C. than a temperature of the catalyst layer, wherein the temperature of the molybdenum compound layer at the time of catalytic oxidation reaction is lower by greater than 0° C. to 40° C. than the reaction temperature, wherein the molybdenum compound comprises molybdenum oxide and an alkali metal or an alkaline earth metal, and wherein, under a flow of a mixed gas at 440° C. composed of a composition containing 75 vol % of air and 25 vol % of water vapor, a molybdenum sublimation amount (μg/NL) of the molybdenum compound is larger than a molybdenum sublimation amount (μg/NL) of the molybdenum composite oxide catalyst.

7. The method according to claim 6, wherein the organic compound is monoolefins having from 4 to 6 carbon atoms and the oxidative dehydrogenation reaction product is a conjugated diene.

8. The method according to claim 6, wherein a difference between the molybdenum sublimation amount of the molybdenum compound and the molybdenum sublimation amount, f the molybdenum composite oxide catalyst is from 0.2 to 6 μg/NL.

9. The method according to claim 6, wherein 20 mass % or more of the molybdenum compound is molybdenum oxide.

10. The method according to claim 6, wherein a molybdenum content in the molybdenum compound layer is 5 mass % or more.

11. The method according to claim 2, wherein a molybdenum content in the molybdenum compound layer is 5 to 100 mass %.

12. The method according to claim 6, wherein a molybdenum content of the molybdenum compound is 1.2 times or more a molybdenum content of the molybdenum composite oxide catalyst.

13. The method according to claim 6, wherein the alkali metal or alkaline earth metal is selected from the group consisting of sodium, potassium, rubidium, cesium, magnesium, and calcium.

14. The method according to claim 6, wherein the alkali metal or alkaline earth metal is selected from the group consisting of sodium, potassium, rubidium, magnesium, and calcium.

* * * * *